United States Patent
Uthgenannt et al.

(10) Patent No.: US 10,603,188 B2
(45) Date of Patent: Mar. 31, 2020

(54) BEARING TRIAL SYSTEM

(71) Applicant: Biomet Manufacturing, LLC, Warsaw, IN (US)

(72) Inventors: Brian Uthgenannt, Winona Lake, IN (US); Paul Meyers, Warsaw, IN (US); Andrew L. Pierce, Warsaw, IN (US); Richard Detlefsen, Fort Wayne, IN (US); David Smith, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/165,127

(22) Filed: May 26, 2016

(65) Prior Publication Data
US 2016/0346098 A1  Dec. 1, 2016

Related U.S. Application Data

(60) Provisional application No. 62/253,804, filed on Nov. 11, 2015, provisional application No. 62/168,053, filed on May 29, 2015.

(51) Int. Cl.
*A61F 2/38* (2006.01)
*A61F 2/46* (2006.01)

(52) U.S. Cl.
CPC ............ *A61F 2/4684* (2013.01); *A61F 2/389* (2013.01); *A61F 2/3859* (2013.01); *A61F 2/3868* (2013.01)

(58) Field of Classification Search
CPC ........ A61F 2/3868; A61F 2/461; A61F 2/389; A61F 2002/2892
See application file for complete search history.

(56) References Cited

U.S. PATENT DOCUMENTS 5,358,530 A * 10/1994 Hodorek ............... A61F 2/3868
                                                        623/20.29
2003/0055500 A1 * 3/2003 Fell .......................... A61F 2/38
                                                        623/14.12

(Continued)

FOREIGN PATENT DOCUMENTS

WO  2016196158  12/2016

OTHER PUBLICATIONS

"International Application Serial No. PCT/US2816/034238, International Search Report dated Sep. 9, 2016", 6 pgs.

(Continued)

*Primary Examiner* — Christopher D. Prone
(74) *Attorney, Agent, or Firm* — Schwegman Lundberg & Woessner, P.A.

(57) ABSTRACT

Systems including a provisional tibial prosthesis system are disclosed. The provisional system can include a tibial component, a base component, and a shim component. The tibial component can have a proximal surface and a distal surface, the distal surface can be configured to seat on a resected proximal surface of a tibia. The base component can have a proximal surface and can be configured to couple with the tibial component when disposed on the proximal surface thereof. The shim component can have a proximal surface and a distal surface. The proximal surface can be configured as an articulating surface sized and shaped to articulate with a femoral prosthesis and the distal surface can be configured to couple with the base component at the proximal surface thereof.

26 Claims, 15 Drawing Sheets

(56) References Cited

U.S. PATENT DOCUMENTS

| | | | |
|---|---|---|---|
| 2008/0051908 A1* | 2/2008 | Angibaud | A61F 2/389 623/20.32 |
| 2012/0158152 A1* | 6/2012 | Claypool | A61F 2/389 623/20.33 |
| 2013/0035694 A1 | 2/2013 | Grimm et al. | |
| 2014/0172112 A1 | 6/2014 | Marter | |
| 2014/0296859 A1 | 10/2014 | Claypool et al. | |
| 2015/0057758 A1* | 2/2015 | Axelson, Jr. | A61F 2/4684 623/20.32 |

OTHER PUBLICATIONS

"International Application Serial No. PCT/US2816/034238, Written Opinion dated Sep. 9, 2016", 5 pgs.
"European Application No. 16728494.2, Response filed Aug. 7, 2018 to Office Action dated Jan. 30, 2018", 15 pgs.
"European Application Serial No. 16728494.2, Communication Pursuant to Article 94(3) EPC dated Nov. 12, 2018", 5 pgs.
"European Application Serial No. 16728494.2, Response Filed Mar. 21, 2019 to Communication Pursuant to Article 94(3) EPC dated Nov. 12, 2018", 7 pgs.

* cited by examiner

BEARING TRIAL SYSTEM

CLAIM OF PRIORITY

This application claims the benefit of U.S. Provisional Patent Application Ser. No. 62/253,804, filed on Nov. 11, 2015, and also claims the benefit of U.S. Provisional Patent Application Ser. No. 62/168,053, filed on May 29, 2015, the benefit of priority of each of which is claimed hereby, and each of which are incorporated by reference herein in its entirety.

FIELD

The present subject matter relates to orthopedic procedures and, more particularly, to prostheses, systems and methods used in knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components.

Provisional knee prosthesis systems, including a plurality of provisional components, can be positioned on a distal end of a femur or a proximal end of a tibia to allow a surgeon to test and appropriately fit a permanent knee prosthesis system within a patient. During surgery, the surgeon can remove and replace various of the provisional components based upon fit and other criteria to arrive at an appropriate configuration of the permanent knee prosthesis system.

Overview

This disclosure pertains generally to provisional tibial prostheses, systems, and methods, including one or more provisional tibial components that can collectively be used to replicate permanent (or final) tibial components. When used provisionally, the tibial prostheses, systems, and methods disclosed herein can assist in determining a proper configuration of a permanent tibial prosthesis system that is designed to replace all or a portion of a knee joint. The present tibial prostheses, systems, and methods can be used in conjunction with one or more permanent tibial prosthesis systems.

The present inventors recognize, among other things, that existing provisional implants, systems, and methods can require a convoluted process where either a high number of provisional components are stacked to arrive at a desired configuration of the permanent tibial prosthesis system and/or the provisional components are not configured for stacking such that components must be inserted into the knee joint than removed therefrom individually if a desired configuration is not achieved. Some provisional systems also require insertion and/or removal tools. Considering these factors, the present inventors propose a simple provisional system that utilizes a minimal number of components including shims that can be stacked together as desired and need not be removed prior to arrive at an appropriate configuration for the permanent tibial prosthesis system. Furthermore, the shims can form a bearing surface of the provisional assembly allowing for ease of insertion (e.g., insertion and/or removal by hand) rather than by the use of a dedicated tool. In some cases, removal can be facilitated by a tool. Ease of insertion or removal can be facilitated in that the shim(s) can be placed upon a base component rather than being inserted between components of the provisional system.

To further illustrate the apparatuses, systems and methods disclosed herein, the following non-limiting examples are provided:

In Example 1, a provisional tibial prosthesis system can comprise a tibial component, a base component, and a shim component. The tibial component can have a proximal surface and a distal surface, the distal surface configured to seat on a resected proximal surface of a tibia. The base component can have a proximal surface and configured to couple with the tibial component when disposed on the proximal surface thereof. The shim component can have a proximal surface and a distal surface, the proximal surface configured as an articulating surface sized and shaped to articulate with a femoral prosthesis and the distal surface configured to couple with the base component at the proximal surface thereof.

In Example 2, the system of Example 1, wherein the proximal surface of the shim component can be substantially a same configuration as the proximal surface of the base component.

In Example 3, the system of Example 2, wherein the distal surface of the shim component can be configured to mate with the proximal surface of the base component.

Example 4, the system of any one or any combination of Example 1-3, wherein the proximal surface of the base component can be sized and shaped to articulate with the femoral prosthesis when the shim component is not utilized with system.

In Example 5, the system of any one or any combination of Examples 1-4, wherein the shim component can comprise at least a first shim component having a first proximal-distal thickness and a second shim component having a second proximal-distal thickness.

In Example 6, the system of Example 5, wherein either of the first or the second shim component can be stackable on the base component, and wherein the second shim component can be configured to be complementary with the first shim component such that the first shim component and the second shim component are stackable together.

In Example 7, the system of Example 5, wherein the first shim component can have substantially a 1 mm proximal-distal thickness and the second shim component has substantially a 2 mm proximal-distal thickness.

In Example 8, the system of Example 5, wherein the first shim component can be configured to be stackable on the second shim component but the second shim component is configured so as not to be stackable on the first shim component.

In Example 9, the system of any one or any combination of Examples 1-8, can further comprise a femoral prosthesis and wherein the shim component can be configured to be inserted between the femoral component and the base component and can be configured to comprise a bearing between the femoral component and the tibial prosthesis system.

In Example 10, the system of any one or any combination of Examples 1-9, wherein the shim component can be configured to be inserted in both an anterior-posterior direction and a proximal-distal direction relative to the base component.

In Example 11, the system of any one or any combination of Examples 1-10, wherein the tibial component and the base component can include complementary mating features configured to couple with one another in a mating engagement.

In Example 12, the system of Example 11, wherein the mating features can comprise projections extending from the proximal surface of the tibial component and one or more recesses that open along the distal surface of the base component.

In Example 13, the system of any one or any combination of Examples 1-12, wherein the shim component and the base component can include complementary mating features configured to couple with one another in a mating engagement.

In Example 14, the system of any one or any combination of Examples 1-13, wherein the base component and the shim component can have corresponding apertures, and wherein the apertures can be configured to generally align with one another when the shim component is coupled to the base component.

In Example 15, a provisional tibial prosthesis system can comprise a set of shim components. Each of the shim components can have a different proximal-distal thickness and having a proximal surface configured as an articulating surface. At least some of the shim components can be configured to be complementary to others of the shim components such that the at least some shim components of the set can be stacked atop others of the shim components to achieve a desired proximal-distal thickness.

In Example 16, the system of Example 15, can further comprise a set of different sized base components.

In Example 17, the system of Example 16, wherein each of the set of shim components can be configured to be complementary to a proximal surface of each of the set of different sized base components.

In Example 18, the system of any one or any combination of Examples 16 and 17, wherein the set of shim components and the set of base components can provide at minimum 11 mm of proximal-distal thickness when coupled together.

In Example 19, the system of any one or any combination of Examples 15-18, wherein the set of different sized shims can comprise at least a first shim component having substantially a 1 mm proximal-distal thickness and a second shim component having substantially a 2 mm proximal-distal thickness.

In Example 20, the system of Example 19, wherein the first shim component can be configured to be stackable on the second shim component but the second shim component is configured so as not to be stackable on the first shim component.

In Example 21, the system of any one or any combination of Examples 15-20, can further comprise a shim handling instrument including an interface configured to engage with an anterior portion of each of the set of shim components.

In Example 22, a provisional tibial prosthesis system can comprise a tibial component, a base component, and a shim component. The tibial component can have a distal surface configured to seat on a resected proximal surface of a tibia. The base component can have a proximal surface and configured to couple with the tibial component when disposed thereon. A shim component can be configured to couple with the base component when disposed thereon and having a proximal surface that is substantially a same configuration as the proximal surface of the base component, wherein either the proximal surface of the base component or the proximal surface of the shim component are sized and shaped to articulate with a femoral prosthesis.

In Example 23, the system of Example 22, wherein a distal surface of the shim component can be configured to mate with and be complementary to the proximal surface of the base component.

In Example 24, the system of any one or any combination of Examples 22 and 23, wherein the shim component can comprise at least a first shim component having a first proximal-distal thickness and a second shim component having a second proximal-distal thickness.

In Example 25, the system of Example 24, wherein either of the first or the second shim component can be stackable on the base component, and wherein the second shim component can be configured to be complementary with the first shim component such that the first shim component and the second shim component are stackable together.

In Example 26, the system of Example 25, wherein the first shim component can have substantially a 1 mm proximal-distal thickness and the second shim component has substantially a 2 mm proximal-distal thickness.

In Example 27, the system of Example 26, wherein the first shim component can be configured to be stackable on the second shim component but the second shim component can be configured so as not to be stackable on the first shim component.

In Example 28, the systems of any one or any combination of Examples 1-27 can optionally be configured such that all elements or options recited are available to use or select from.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to tibial prostheses, systems, and methods. The systems, for example, can comprise a provisional tibial prosthesis system that includes a provisional tibial component, a base component, and one or more provisional shim components. The shim components can be used as a height varying spacer and as an articular bearing between the provisional tibial prosthesis system and a femoral component. One or more of the shim components can be added to the remainder of the provisional tibial prosthesis system to alter a spacing between the provisional tibial prosthesis system and the femoral component. This adjustment can be used to simulate a permanent tibial prosthesis systems and other prostheses.

Figure 1:
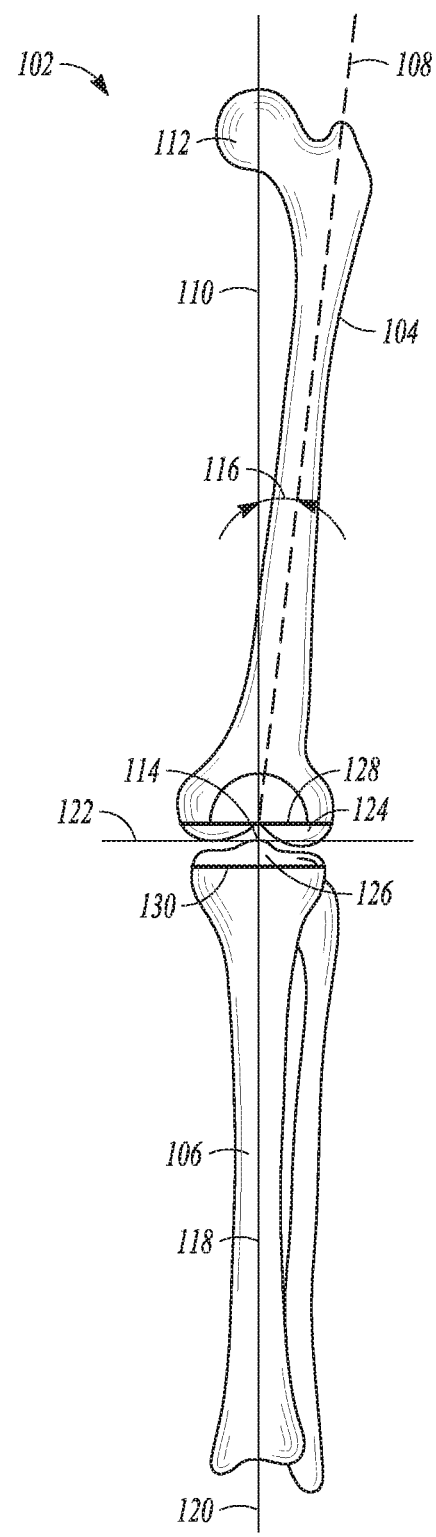
FIGS. 1 and 2 illustrate knee joint structures providing suitable environments in which a provisional tibial prosthesis system in accordance with an example of the present application can be utilized.
Figure 2:
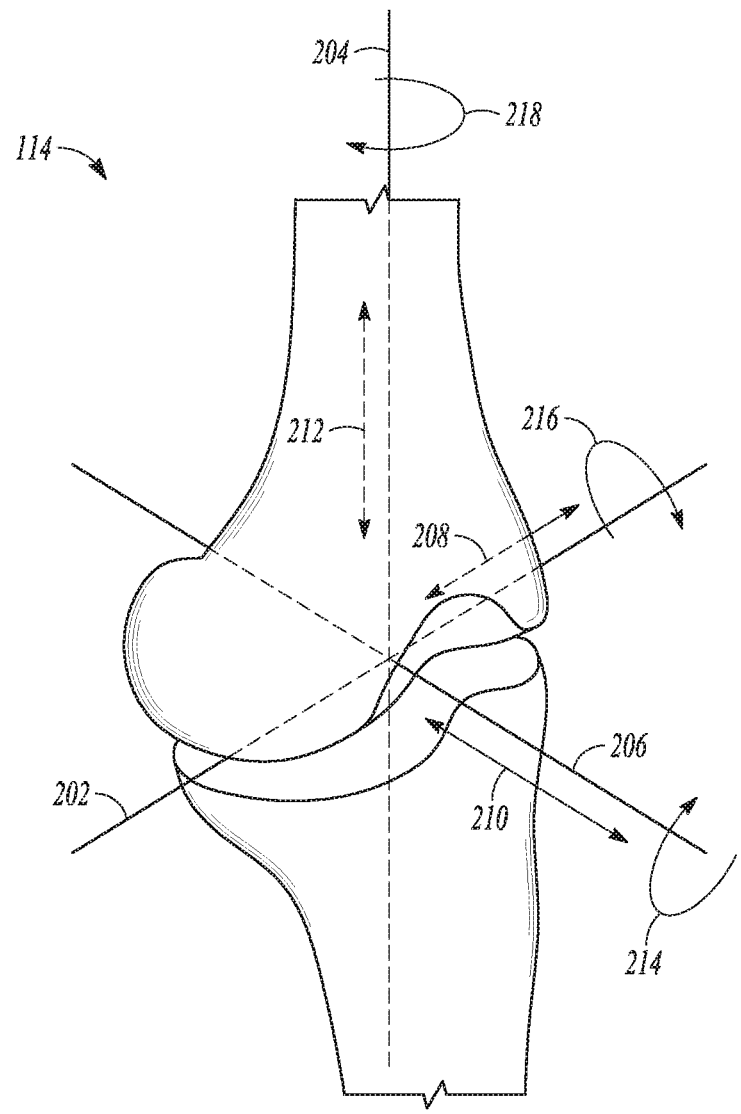

To better understand knee joint replacement procedures, it can be helpful to understand the relationship of bones and bone cuts that can be made to orient various provisional and permanent prosthesis components within a knee joint. FIGS. 1 and 2 illustrate several features of knee joint structures and orientations. In FIG. 1, a frontal view of a lower limb 102, including a femur 104 and a tibia 106, is shown to illustrate various lower limb axes. The femur 104 has an anatomic axis 108 that coincides generally with its intramedullary canal. The femur 104 also has a mechanical axis 110, or load axis, running from the center of a femoral head 112 to the center of a knee joint 114. The angle 116 extending between these two axes varies among the patient population, but is generally on the order of between 5-7 degrees, inclusive. Like the femur 104, the tibia 106 also has an anatomic axis coinciding generally with its intramedullary canal. The mechanical axis 118 of the tibia 106 runs from the center of the knee joint 114 to the center of an ankle region 120 and is generally collinear with its anatomic axis.

A joint line 122, about which the knee joint 114 flexes, is approximately parallel to a line through medial and lateral femoral condyles 124 and to a tibial plateau 126. Although illustrated as perpendicular in FIG. 1, the joint line 122 can extend at a varus or valgus angle relative to the mechanical axes 110 and 118 of the femur 104 and tibia 106, respectively. Normally, during a partial or total knee replacement procedure, portions of a distal end of the femur 104 or a proximal end of the tibia 106 are resected to be parallel or approximately parallel to the joint line 122, and thus perpendicular to the mechanical axes 110 and 118, as indicated at 128 and 130, respectively.

FIG. 2 illustrates a closer view of the knee joint 114 and its coordinate system, in which a medial/lateral axis 202 corresponds approximately to the joint line 122 (FIG. 1), a proximal/distal axis 204 corresponds approximately to the mechanical axes 110 and 118 (FIG. 1), and an anterior/posterior axis 206 is approximately normal to the other two axes. Position along each of these axes can be depicted by arrows, which can represent the medial/lateral 208, anterior/posterior 210, and proximal/distal 212 positioning of inserted prosthesis components. Rotation about each of these axes can also be depicted by arrows. Rotation about the proximal/distal axis 204 can correspond anatomically to external rotation of a femoral component, while rotation about the anterior/posterior axis 206 and medial/lateral axis 202 can correspond to extension plane slope and varus/valgus angle of a component, respectively. Depending on a position of the proximal tibial cut 130 (FIG. 1) made, a varus/valgus angle 214, extension plane angle 216, external rotation 218, or joint extension gap can be affected. Similarly, a position of the distal femoral cut 128 (FIG. 1) can affect the location of the joint line 122, the extension gap, the varus/valgus angle 214, or the extension plane angle 216.

As used herein, "proximal" refers to a direction generally toward the torso of a patient, and "distal" refers to the opposite direction of proximal, i.e., away from the torso of a patient. "Anterior" refers to a direction generally toward the front of the patient, and "posterior" refers to the opposite direction of anterior, i.e., toward the rear of the patient.

Figure 3A:
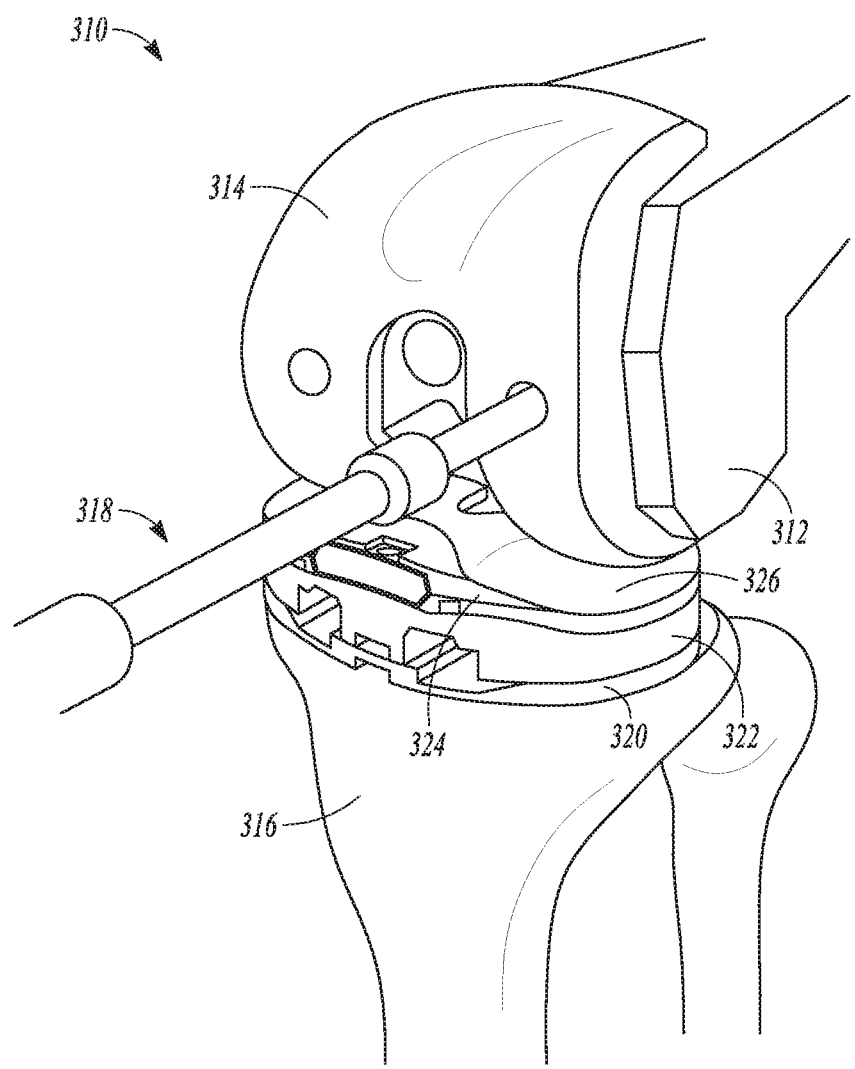
FIG. 3A illustrates a knee joint structure, a femoral prosthesis, and a provisional tibial prosthesis system in accordance with an example of the present application.

FIG. 3A illustrates a knee joint 310 structure including a femur 312, a femoral component 314, a tibia 316, and a provisional tibial prosthesis system 318. The provisional tibial prosthesis system 318 can include a tibial component 320, a base component 322, and a shim component 324 according to the illustrated example.

Figure 3B:
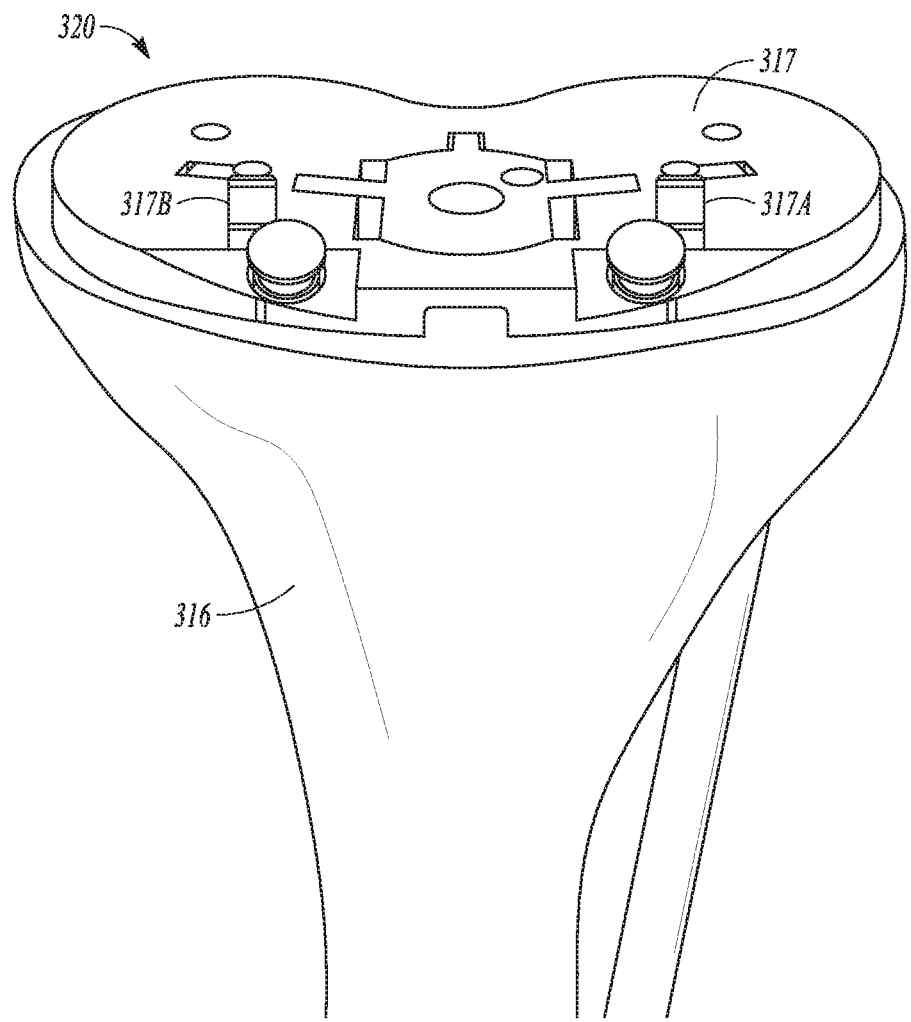
FIG. 3B illustrates a tibial component of the provisional tibial prosthesis system of FIG. 3A mounted to a resected tibia in accordance with an example of the present application.

As shown, the femoral component 314 can be disposed at a resected distal surfaces of the femur 312. The provisional tibial prosthesis system 318 can be disposed at a resected proximal end of the tibia 316. In particular, the tibial component 320 of the provisional tibial prosthesis system 318 can be configured to seat on a resected proximal surface of the tibia 316 as shown in FIGS. 3A and 3B, and can be configured to couple with the base component 322 which can be mounted thereon as shown in FIG. 3A. Thus, the base component 322 can be configured to couple with the tibial component 320 when disposed thereon. The shim component 324 can have a proximal surface 326 and a distal surface (see FIG. 3C). The proximal surface 326 can be configured as an articulating surface (i.e. is shaped to interface with and be generally complementary to the femoral prosthesis 314 as the femoral prosthesis 314 moves in flexion and extension relative to the provisional tibial prosthesis system 318) with the femoral prosthesis 314 as shown in FIG. 3A. The distal surface of the shim component 324 can be configured to couple with the base component 322 at the proximal surface thereof as shown in FIG. 3A.

The shim component 324 can be used as a height varying spacer and articular bearing between the provisional tibial prosthesis system 314 and the femoral component 312. One or more of the shim components 324 can be added to the remainder of the provisional tibial prosthesis system 318 to alter a spacing between the provisional tibial prosthesis system 318 and the femoral component 314. This adjustment can be used to simulate permanent tibial prosthesis systems and other prostheses. The provisional tibial prosthesis system 318 can also allow a physician to determine a desired thickness of permanent prosthesis by allowing for adjustment (e.g., by adding or removing the shim component 324 from the provisional tibial prosthesis system 318) following one or more tests that can test a range of motion of the knee joint, for example.

As will be shown and discussed subsequently, the shim component 324 can be inserted between the femoral component 314 and the base component 322 and can be configured to comprise a bearing between the femoral component 314 and the provisional tibial prosthesis system 318. According to some examples, the shim component 324 may not be used with the base component 322 and the tibial component 320 (e.g., a desired thickness is achieved without the need of the shim component 324). In such examples, the base component 322 can have a proximal surface 328 (FIG. 3C) configured as an articulating surface with the femoral component 314 in a similar manner to that of the proximal surface 326 of the shim component 324.

FIG. 3B shows the tibial component 320 mounted on resected proximal surface of the tibia 316 with other components of the provisional tibial prosthesis system 318 removed. The tibial component 320 can include a proximal surface 317 and base component mating features 317A and 317B (e.g., projections).

Figure 3C:
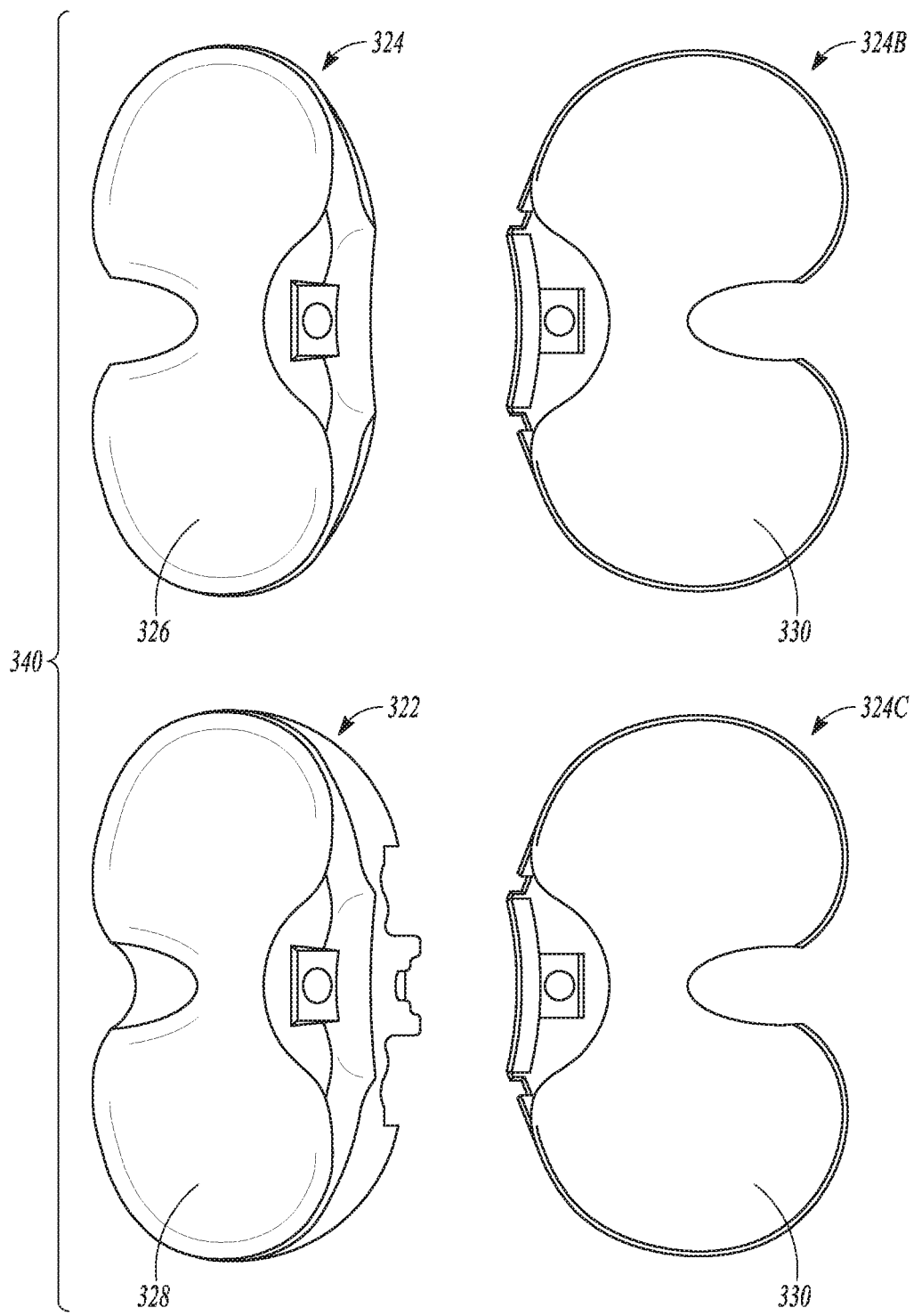
FIG. 3C illustrates various components of the provisional tibial prosthesis system of FIG. 3A as disassembled in accordance with an example of the present application.

According to some examples such as the one illustrated in FIG. 3C, the proximal surface 326 of the shim component 324 can have substantially a same configuration (e.g., proximal surface shape) as the proximal surface 328 of the base component 322. Thus, the proximal surfaces 326, 328 of both the shim component 324 and the base component 322 can be identical in configuration such that either can act as the articular surface with a particular geometry. Furthermore, as shown in FIG. 3C, a distal surface 330 of the shim component 324 can be configured to mate with and be complementary to the proximal surface 328 of the base component 322.

As is further shown in the example of FIG. 3C, the shim component 324 and the base component 322 can comprise a sub-system 340 where the shim component 324 comprises a plurality of shim components 324A, 324B, 324C. The plurality of shim components 324A, 324B, 324C can have a similar design as one another save for a proximal-distal thickness, which can differ. For example, the shim components 324A, 324B can have a 2 mm proximal-distal thickness while the shim component 324C can have a 1 mm proximal-distal thickness. The thickness values provided are exemplary and can vary as desired. According to some examples, the shim component 324C can be configured to be stackable on the shim component 324A, 324B but the shim component 324C can is configured so as not to be stackable on itself (i.e. two shim components having 1 mm proximal-distal thickness may not be stackable on one another or the shim component(s) 324A, 324B may not be stackable on shim component 324C).

Figure 4A:
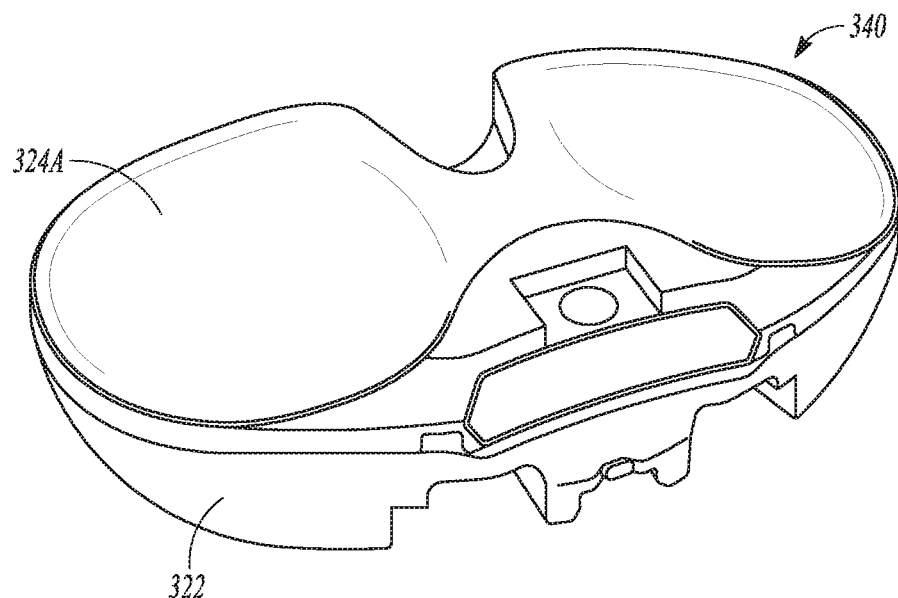
FIGS. 4A and 4B show a base component coupled with shim component(s) in accordance with an example of the present application.
Figure 4B:
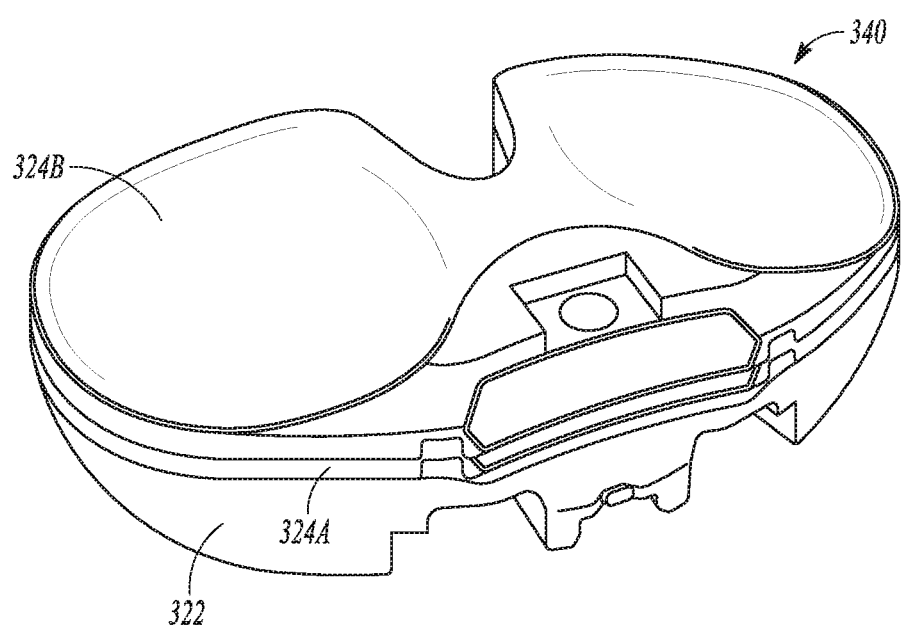

FIGS. 4A and 4B illustrate the sub-system 340 where the shim components 324A, 324B can be stacked atop one another as shown in FIG. 4B and/or can be stacked atop the base component 322 (FIGS. 4A and 4B). As such, the shim components 324A, 324B can be used as a height varying spacer and articular bearing between the provisional tibial prosthesis system 314 and the femoral component 312. In particular, FIG. 4A shows an example where the shim component 324A is stacked atop (mounted to) the base component 322 and FIG. 4B shows an example where the shim component 324B has been further added to the sub-system 340 of FIG. 4A and is stacked (mounted to) atop the shim component 324A.

According to some examples, the sub-system 340 can further include a set of different sized base components (e.g., a base component with a 10 mm proximal-distal thickness and a second base component with a 16 mm proximal-distal thickness). In such cases, each of the set of shim components (e.g., shim components 324A, 324B) can be configured to be complementary to a proximal surface of each of the set of different sized base components. According to one example, the set of shim components and the set of base components can provide at minimum 11 mm of proximal-distal thickness when coupled together (e.g., the base component can provide 10 mm proximal-distal thickness and single shim component can have a 1 mm proximal-distal thickness).

Figure 5A:
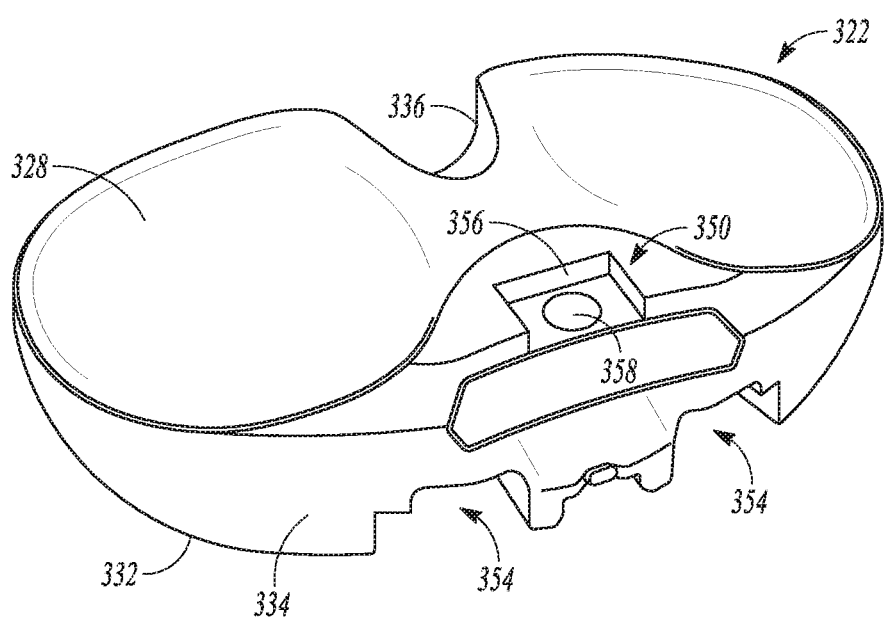
FIGS. 5A to 5C show the base component of the provisional tibial prosthesis system of FIGS. 4A and 4B in accordance with an example of the present application.
Figure 5B:
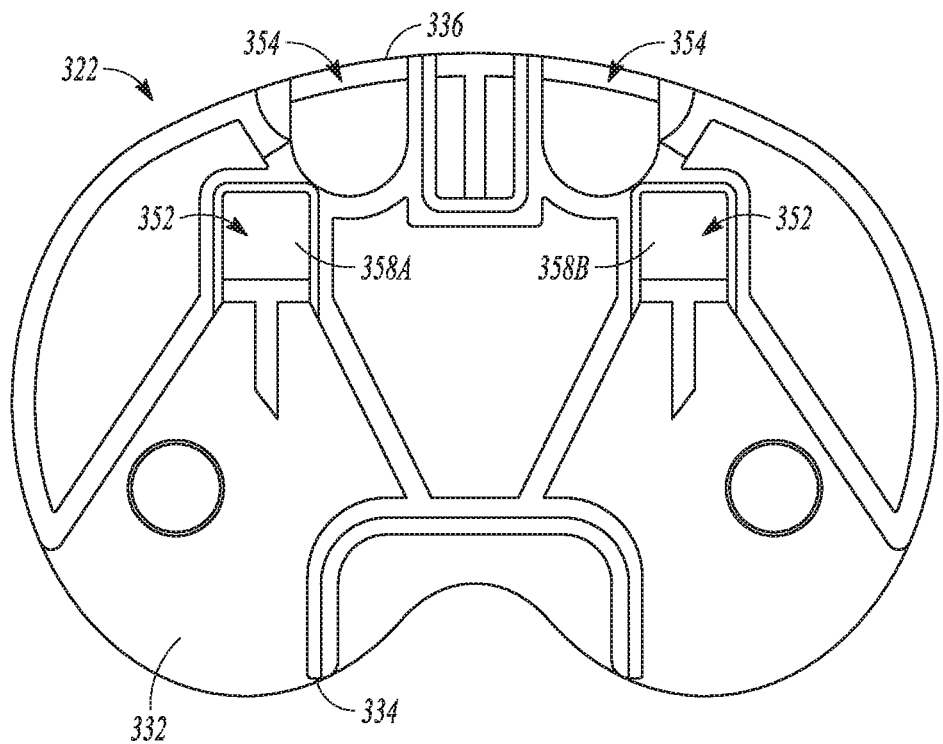
Figure 5C:
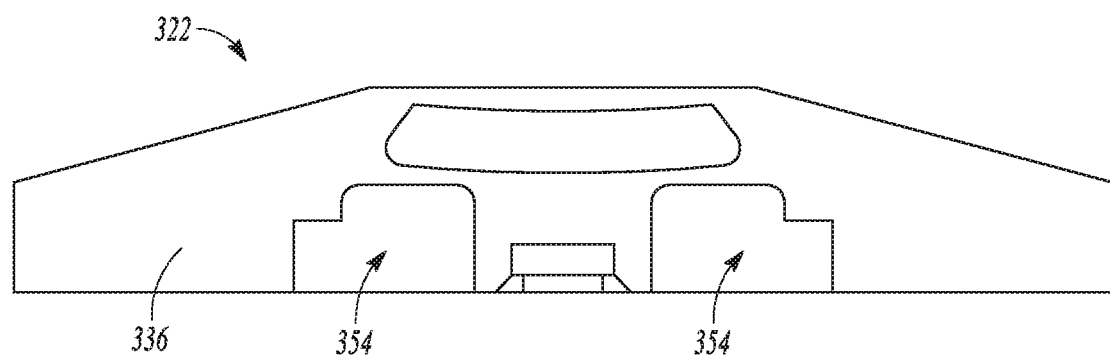

FIGS. 5A to 5C show the base component 322 according to one example. As was discussed previously, the base component 322 includes a proximal surface 328 (FIG. 5A), a distal surface 332, an anterior periphery 334, and a posterior periphery 336. The base component 322 can additionally include a shim mating feature 350 and a tibial component mating feature 352 (FIG. 5B).

The proximal surface 328 generally opposes the distal surface 332 and extends from the anterior periphery 334 to the posterior periphery 336. As discussed previously, the proximal surface 328 can be configured as an articular surface to articulate with the femoral component in instances where a shim component may not be desired. As such, the proximal surface 328 can be dished shaped and can generally have a medial compartment and a lateral compartment as illustrated in FIG. 5A.

According to the example of FIGS. 5A to 5C, the anterior periphery 334 can be provided with recesses 354. The recesses 354 can aid in mounting the base component 322 to the tibial component (not shown) by coupling with an insertion and/or removal tool. According to further examples, the recesses 354 can provide access to the tibial component (not shown) as desired and can serve other purposes such as when used with a permanent tibial tray component. The posterior periphery 336 can vary so as to form a PCL cutout such as in the cruciate-retaining type design as illustrated.

The shim mating feature 350 can be positioned at the proximal surface 328 at or adjacent the anterior periphery 334 as shown in FIG. 5A. According to the example of FIG. 5A, the shim mating feature 350 can comprise a female feature such as a recess 356 configured to mate with a male projection of the shim component 324 (FIG. 6B). As shown in FIG. 5A, the shim mating feature 350 can additionally include an aperture 358.

FIG. 5B provides further illustration of the distal surface 332 and the tibial component mating feature 352. In FIG. 5B, the tibial component mating feature 352 can comprise recesses 358A and 358B configured to receive and couple with the base component mating features 317A and 317B (FIG. 3B). The distal surface 332 can be configured to seat on the proximal surface 317 of the tibial component 320 (FIG. 3B).

Figure 6A:
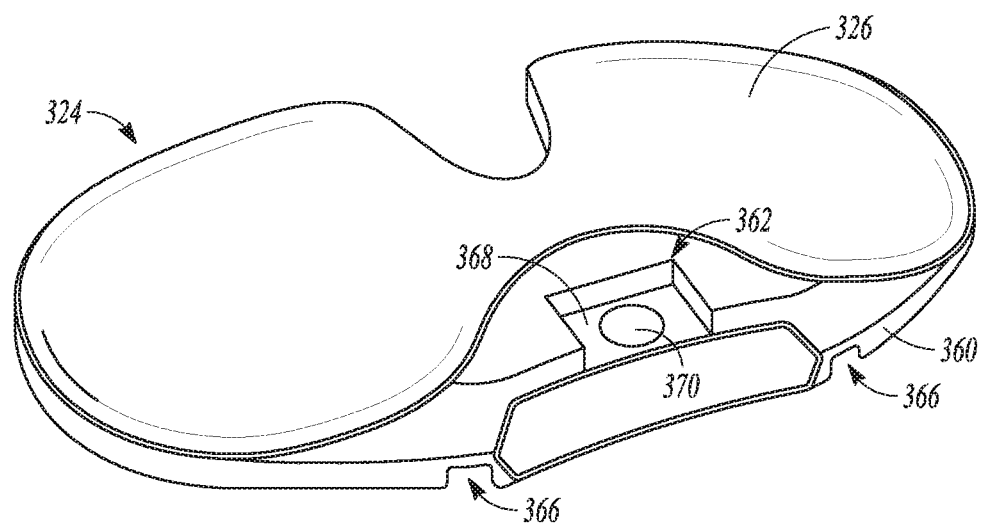
FIGS. 6A and 6B show the shim component of the provisional tibial prosthesis system in accordance with an example of the present application.
Figure 6B:
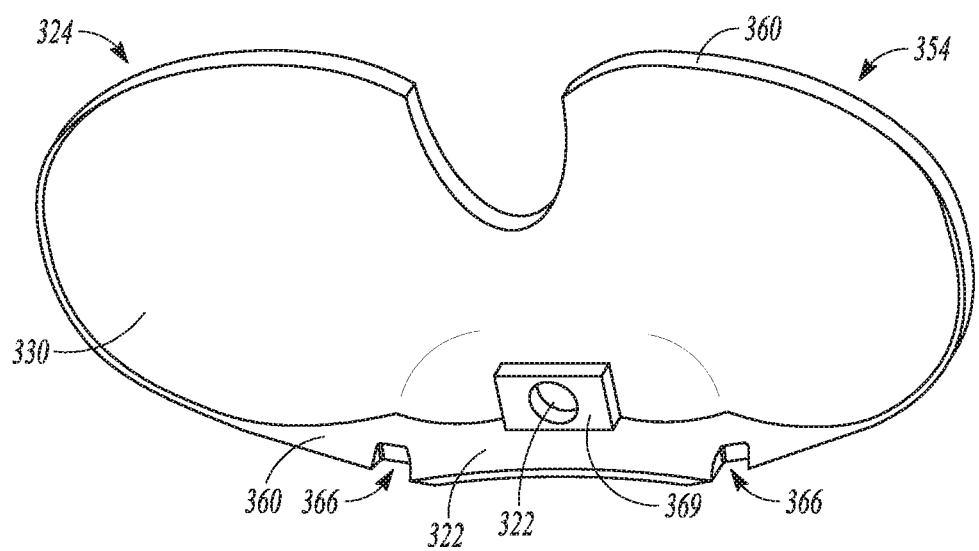
Figure 7A:
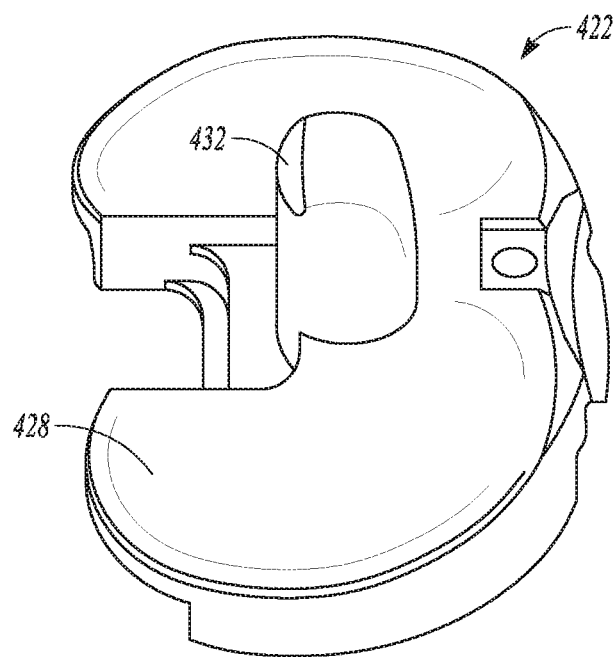
FIGS. 7A to 7C show a base component of another provisional tibial prosthesis system in accordance with an example of the present application.
Figure 7B:
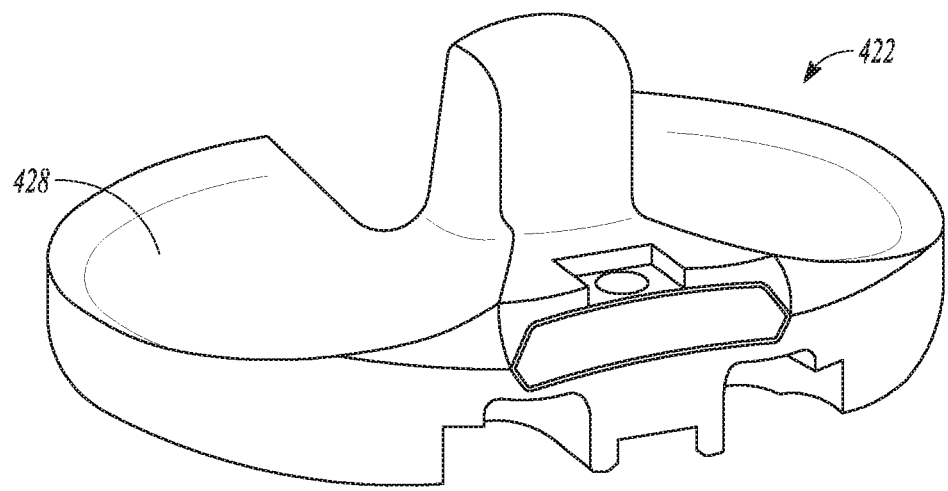
Figure 7C:
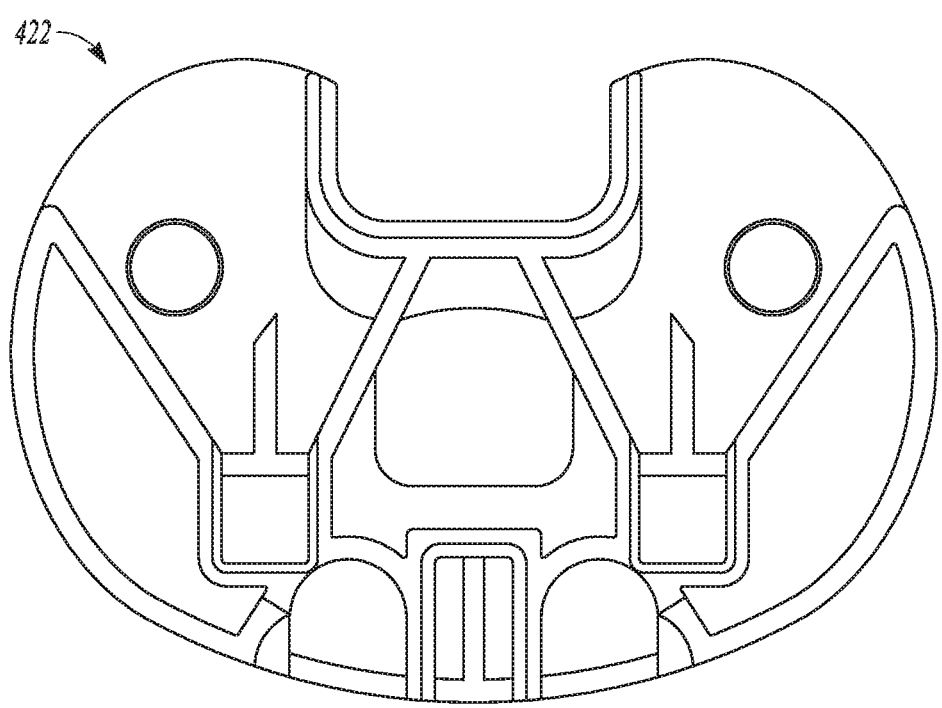
Figure 8A:
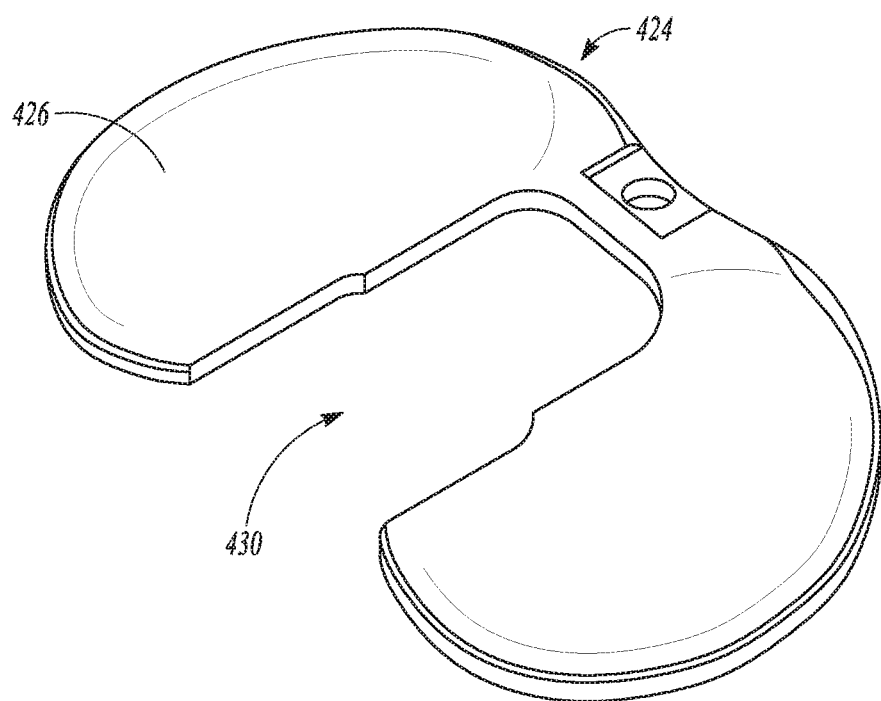
FIGS. 8A and 8B show a shim component compatible with the base component of FIGS. 7A to 7C in accordance with an example of the present application.
Figure 8B:
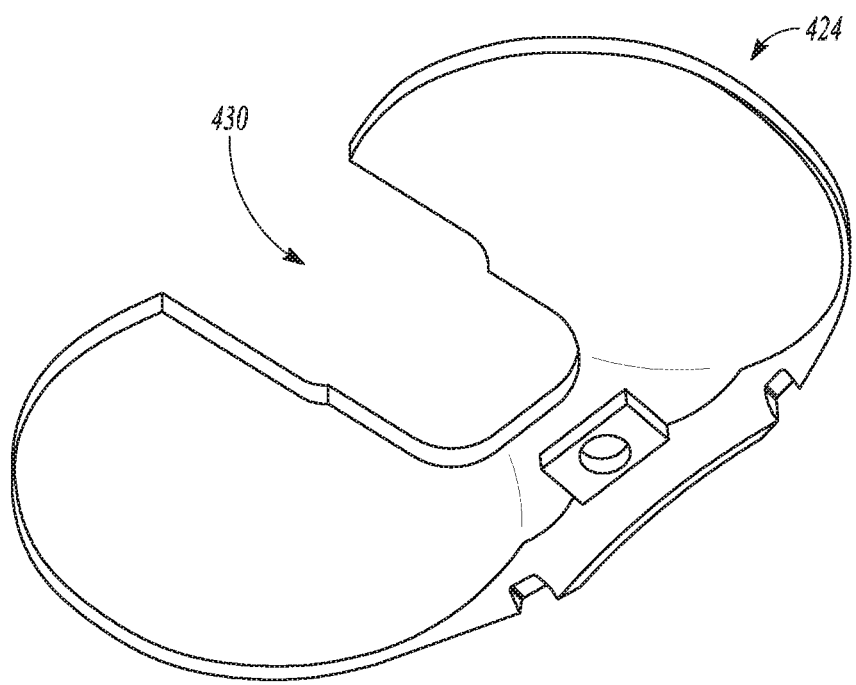

FIGS. 6A and 6B show the shim component 324 according to one example. As previously discussed, the shim component 324 can include the proximal surface 326 and the distal surface 330. The shim component 324 can additionally include a peripheral projection 360, a first mating feature 362, a second mating feature 364, and notches 366.

The peripheral projection 360 can extend about the distal surface 330 as shown in FIG. 6B. The projection 360 can extend further distally toward an anterior of the shim component 324 and can be of a smaller distal extent along the lateral, medial, and posterior sides of the shim component. The shim component 324 can be sized and configured such that the projection 360 is positioned to interface with and extend along an outer periphery of the base component 322 (FIG. 5A). Although illustrated as extending around substantially an entire periphery of the shim component 324 in the example of FIGS. 6A and 6B, according to further examples, the projection 360 may occur only in certain portion (e.g., along the anterior portion) of the shim component 324.

Similar to corresponding features of the base component 322 (see e.g., FIGS. 3C and 5A), the first mating feature 362 can be positioned at the proximal surface 326 at or adjacent an anterior portion of the shim component 324 as shown in FIG. 6A. According to the example of FIG. 6A, the first mating feature 362 can comprise a female feature such as a recess 368 configured to mate with a male projection of a second shim component. Such a male projection 369 is illustrated in FIG. 6B, and comprises part of the second mating feature 364. The male projection 370 is also configured to be received by and couple with the shim mating feature 350 of the base component 322 (FIG. 5A).

As shown in FIGS. 6A and 6B, the shim component 324 can include an aperture 370 that extends therethrough and is located at the first mating feature 362 and the second mating feature 364. The aperture 370 can generally align with the aperture 358 of the base component 322 (FIG. 5A) when the shim component 324 is mounted thereon. The apertures 370, 358 can be configured to receive a pin or similar fastener or coupling feature to further couple the shim component 324 to the base component 322 (and to further couple any additional shim components that may be utilized).

The notches 366 can be formed by the peripheral projection 360 at the anterior portion thereof. The notches 366 can be configured to receive portions of a removal tool as will be discussed subsequently.

FIGS. 7A, 7B, 7C, 8A, and 8B show a base component 422 and a shim component 424 configured as a posterior-stabilized type design. As such, the shim component 424 has a relatively larger posterior cutout 430 that accommodates a stem 432 of the base component 422. While the shape of the base component 422 and shim component 424 is somewhat altered from the posterior-stabilized type design of the previous figures, the general arrangement, structures, features, and/or techniques previously described can remain substantially the same with respect to the base component 422 and the shim component 424. Thus, these components will not be described in great detail. It should be noted that the general arrangement, structures, features, and/or techniques previously described can be applicable to base component and shim component designs not specifically shown herein (e.g., to a ultra-congruent type design).

As with the prior described examples, the shim component 424 can be used as a height varying spacer and articular bearing between a provisional tibial prosthesis system and a femoral component. One or more of the shim components 424 can be added to the remainder of the provisional tibial prosthesis system to alter a spacing between the provisional tibial prosthesis system and the femoral component. This adjustment can be used to simulate permanent tibial prosthesis systems and other prostheses.

According to some examples, the shim component 424 may not be used with the base component 422 and the tibial component (not shown) (e.g., a desired thickness is achieved without the need of the shim component 424). In such examples, a proximal surface 428 (FIGS. 7A and 7B) of the base component 422 can act and can be configured as an articulating surface with the femoral component in a manner similar to that of a proximal surface 426 (FIG. 8A) of the shim component 424.

Figure 9:
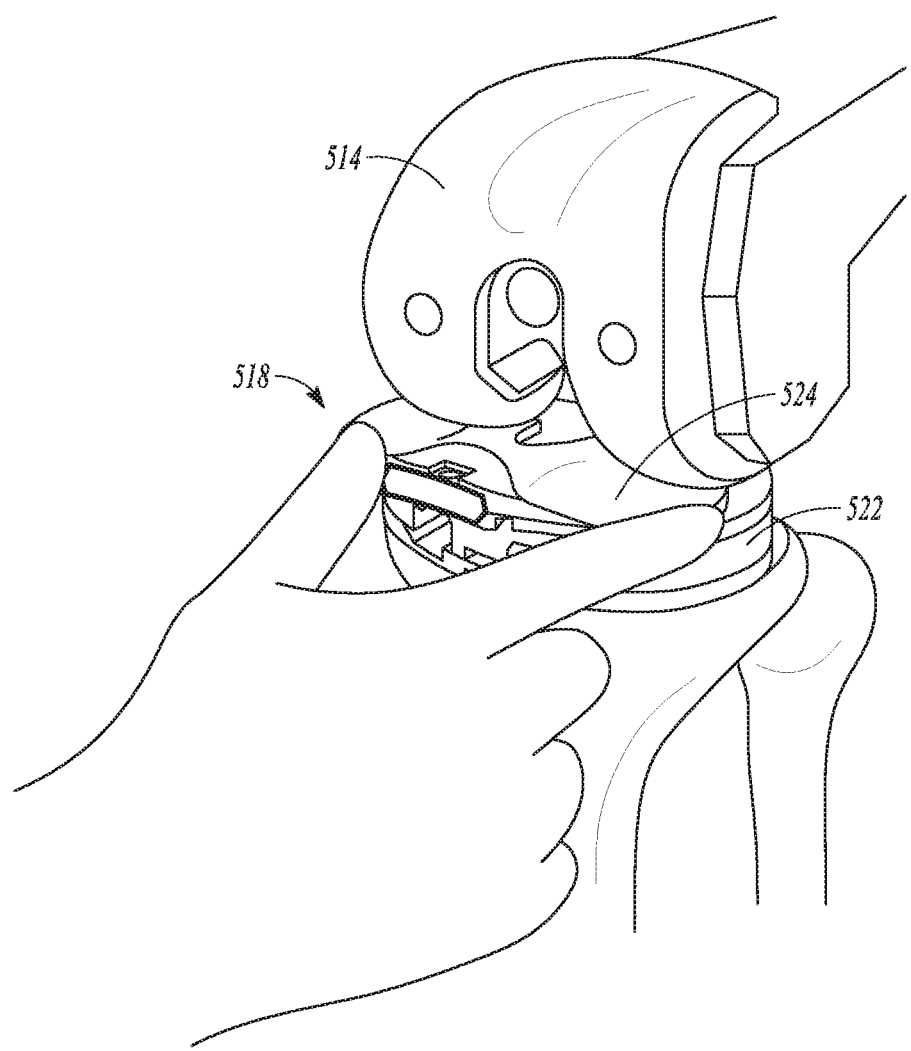
FIG. 9 shows an example of coupling a shim component to a base component of a provisional tibial prosthesis system in accordance with another example of the present application.
Figure 10:
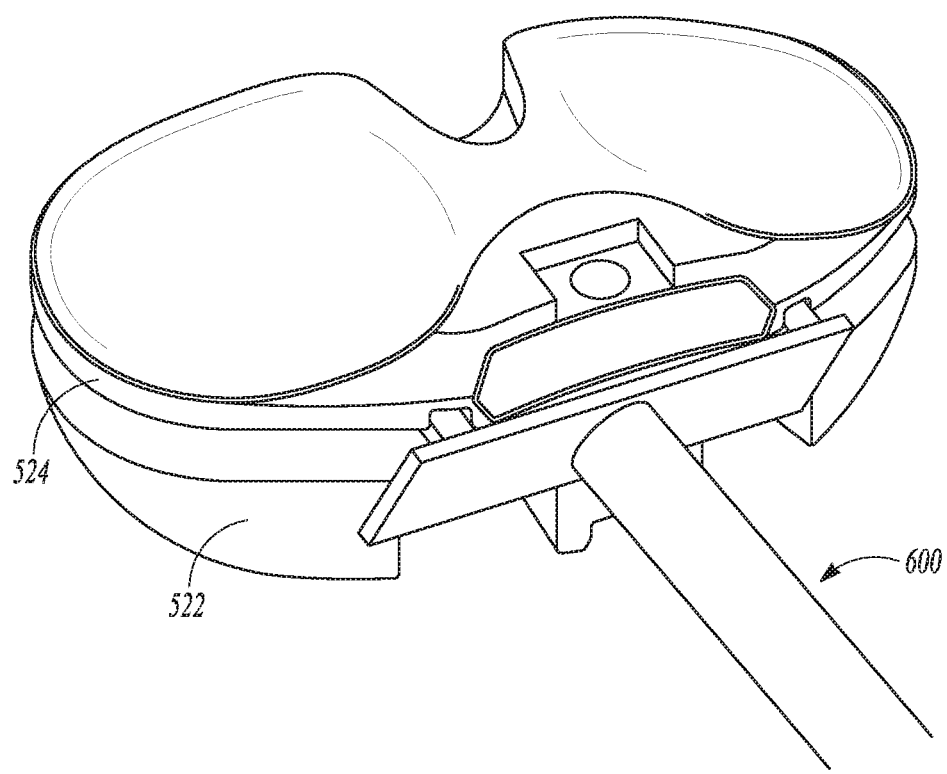
FIG. 10 shows an example of decoupling a shim component from a base component of a provisional tibial prosthesis system with a tool in accordance with another example of the present application.

FIG. 9 illustrates that according to some examples a shim component 524 can be inserted between a femoral component 514 and a base component 522 of a provisional tibial system 518. The insertion can bring the shim component 524 into coupling engagement with the base component 522. As shown in FIG. 9, the insertion can be accomplished by hand or by a tool 600 as shown in FIG. 10. The shim component 524 can be configured to be inserted in both an anterior-posterior direction and a proximal-distal direction relative to the base component 522 as is generally shown. FIG. 10 shows the tool 600 engaging notches on an anterior portion of the shim component 524. According to some examples, the tool 600 can be utilized for one or both inserting and removing the shim component 524 to/from the base component 522. According to other examples, the tool 600 can be used solely for removing the shim component 524 from the base component 522.

Figure 11A:
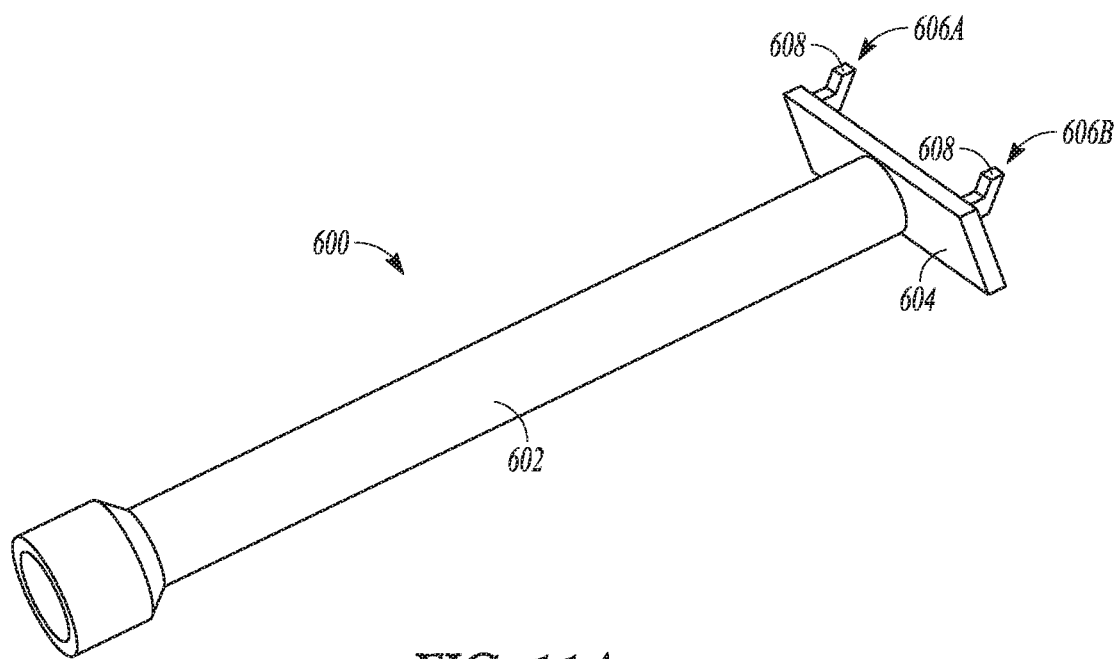
FIGS. 11A and 11B are perspective views of an exemplary tool for coupling and/or decoupling the shim component with the base component in accordance with another example of the present application.
Figure 11B:
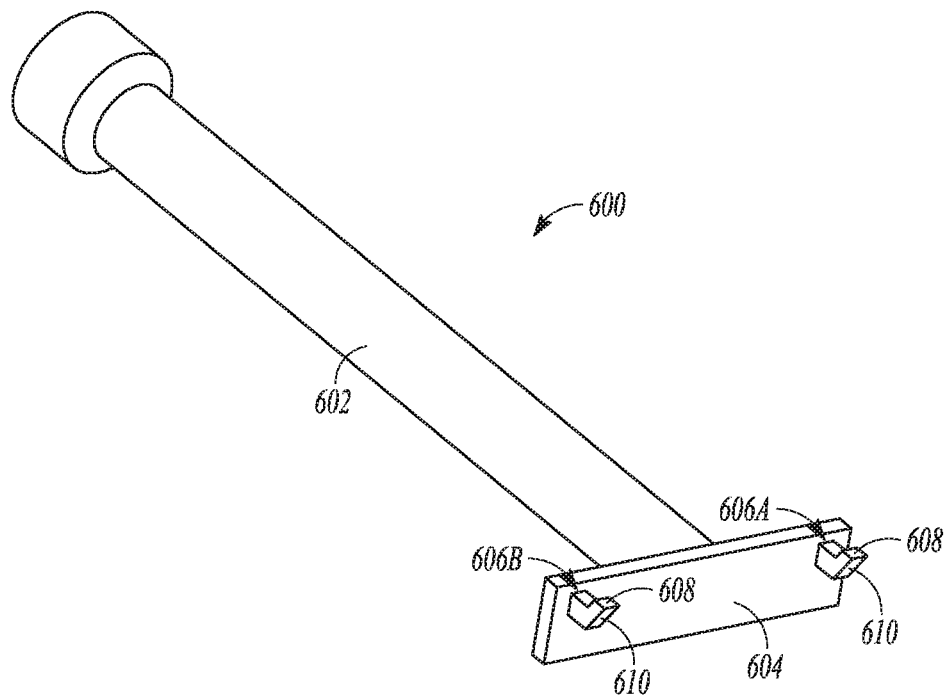

FIGS. 11A and 11B show the tool 600 in further detail. The tool 600 can include a handle 602, a distal plate 604, and projections 606A and 606B. The projections 606A, 606B can each include a hooked portion 608. The hooked portion 608 include an outer surface 610 (FIG. 11B).

The handle 602 can be coupled to the distal plate 604 at a distal end thereof. The projections 606A and 606B can couple to the distal plate 604 on an opposing distal side of the distal plate 604 from the handle 602. The projections 606A and 606B can extend generally distally and the hooked portions 608 thereof can extend in a second direction from the generally proximal-distal extent of the handle 602 and the base of the projections 606A and 606. The outer surface 610 of the hooked portion 606A and 606B can be angled so as to generally correspond to and slide along an outer periphery of the base component 522 and/or another shim component 524. As previously described, the projections 606A and 606B can be configured to engage with notches or other female features to facilitate inserting and/or or removing of the shim component 524.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A provisional prosthesis system comprising:
   a tibial component having a proximal surface and a distal surface, the distal surface configured to seat on a resected proximal surface of a tibia;
   a base component having a proximal surface and configured to couple with the tibial component when disposed on the proximal surface thereof; and
   a shim component having a proximal surface and a distal surface, the proximal surface of the shim component is configured as an articulating surface sized and shaped to articulate with a femoral prosthesis and the distal surface of the shim component is configured to couple with the base component at the proximal surface thereof, wherein the proximal surface of the shim component is substantially a same size and shape as the proximal surface of the base component, and wherein the shim component is configured such that when the shim component is stacked atop the base component a periphery of the shim component is positioned to couple with and extend along a periphery of the base component;
   wherein the proximal surface of the base component is sized and shaped to articulate with the femoral prosthesis when the shim component is not coupled to the base component, wherein the distal surface of the shim component is configured to mate with and be complimentary to the proximal surface of the base component and the shim component has a first mating feature configured to couple with a complimentary second mating feature of the base component such that the shim component is stackable on the base component to change a proximal distal thickness of the system.

2. The system of claim 1, wherein the shim component has a first proximal-distal thickness and further comprising a second shim component having a second proximal-distal thickness.

3. The system of claim 2, wherein either of the shim component or the second shim component is stackable on the base component, and wherein the second shim component is configured to be complementary with the shim component such that the shim component and the second shim component are stackable together.

4. The system of claim 2, wherein the shim component has substantially a 1 mm proximal-distal thickness and the second shim component has substantially a 2 mm proximal-distal thickness.

5. The system of claim 2, wherein the shim component is configured to be stackable on the second shim component but the second shim component is configured so as not to be stackable on first shim component.

6. The system of claim 1, further comprising the femoral prosthesis and wherein the shim component is configured to be inserted between the femoral component and the base component and is configured to comprise a bearing between the femoral component and the tibial prosthesis system.

7. The system of claim 1, wherein the shim component is configured to be inserted in both an anterior-posterior direction and a proximal-distal direction relative to the base component.

8. The system of claim 1, wherein the tibial component and the base component include complementary mating features configured to couple with one another in a mating engagement.

9. The system of claim 8, wherein the mating features comprise projections extending from the proximal surface of the tibial component and one or more recesses that open along the distal surface of the base component.

10. The system of claim 1, wherein the second mating feature of the base component and the first mating feature of the shim component have corresponding apertures, and wherein the apertures are configured to align with one another when the shim component is coupled to the base component.

11. The system of claim 1, wherein the periphery of shim component s formed in part by a projection extending from distal surface.

12. The system of claim 1, wherein when the shim component is stacked atop the base component, the periphery of the shim component aligns with the periphery of the base component.

13. A provisional prosthesis system comprising:
    a femoral component;
    a set of different sized base components; and
    a set of shim components, each of the shim components having a different proximal-distal thickness and having a proximal surface configured as an articulating surface with the femoral component during knee joint movement, wherein the proximal surface of the set of shim components is substantially a same size and shape as a proximal surface of at least some of the set of base components, wherein the at least some of the shim components are configured such that when the at least some shim components are stacked atop the others of the shim components a periphery of the at least some of the shim components is positioned to couple with and extend along a periphery of the others of the shim components, wherein at least some of the shim components have a distal surface configured to mate with and be complimentary to a proximal surface of others of the shim components and the at least some of the shim components have a first mating feature configured to couple with a complimentary second mating feature of the others of the shim components such that the at least some shim components of the set are stackable atop the others of the shim components to achieve a desired proximal-distal thickness.

14. The system of claim 13, wherein the at least some of the shim components of the set of shim components and one of the set of base components can be used in combination to provide at minimum 11 mm of proximal-distal thickness when coupled together.

15. The system of claim 13, wherein the set of different sized shims comprise at least a first shim component having substantially a 1 mm proximal-distal thickness and a second shim component having substantially a 2 mm proximal-distal thickness.

16. The system of claim 15, wherein the first shim component is configured to be stackable on the second shim component but the second shim component is configured so as not to be stackable on the first shim component.

17. The system of claim 13, further comprising a shim handling instrument including an interface configured to engage with an anterior portion of each of the set of shim components.

18. The system of claim 13, wherein the periphery of each of the at least some of the shim components is formed in part by a projection extending from distal surface.

19. The system of claim 13, wherein when the one or more of the shim components are stacked on one or more of the set of base components, the periphery of one or more of the set of shim components aligns with a periphery of one or more of the set of base components.

20. A provisional tibial prosthesis system comprising:
a tibial component having a distal surface configured to seat on a resected proximal surface of a tibia;
a base component having a proximal surface and configured to couple with the tibial component when disposed thereon; and
a shim component having a proximal surface that is substantially a same size and shape as the proximal surface of the base component, wherein both the proximal surface of the base component and the proximal surface of the shim component are sized and shaped to articulate with a femoral prosthesis;
wherein a distal surface of the shim component is configured to mate with and be complimentary to the proximal surface of the base component and the shim component has a first mating feature configured to couple with a complimentary second mating feature of the base component such that the shim component is stackable on the base component to change a proximal distal thickness of the system, wherein the shim component is configured such that when the shim component is stacked atop the base component, a periphery of the shim component is positioned to couple with and extend along a periphery of the base component.

21. The system of claim 20, wherein the shim component has a first proximal-distal thickness and a second shim component having a second proximal-distal thickness.

22. The system of claim 21, wherein either of the shim component or the second shim component is stackable on the base component, and wherein the second shim component is configured to be complementary with the shim component such that the shim component and the second shim component are stackable together.

23. The system of claim 22, wherein the shim component has substantially a 1 mm proximal-distal thickness and the second shim component has substantially a 2 mm proximal-distal thickness.

24. The system of claim 23, wherein the shim component is configured to be stackable on the second shim component but the second shim component is configured so as not to be stackable on the shim component.

25. The system of claim 20, wherein the periphery of shim component is formed in part by a projection extending from distal surface.

26. The system of claim 20, wherein when the shim component is stacked atop the base component, the periphery of the shim component aligns with the periphery of the base component.

* * * * *

UNITED STATES PATENT AND TRADEMARK OFFICE
CERTIFICATE OF CORRECTION

PATENT NO. : 10,603,188 B2
APPLICATION NO. : 15/165127
DATED : March 31, 2020
INVENTOR(S) : Uthgenannt et al.

Page 1 of 1

It is certified that error appears in the above-identified patent and that said Letters Patent is hereby corrected as shown below:

On the Title Page

In Column 2, under "Other Publications", Line 1, delete "PCT/US2816/034238," and insert --PCT/US2016/034238,-- therefor On page 2, in Column 1, under "Other Publications", Line 1, delete "PCT/US2816/034238," and insert --PCT/US2016/034238,-- therefor In the Claims In Column 12, Line 45, in Claim 11, delete "s" and insert --is-- therefor Signed and Sealed this
Eighteenth Day of August, 2020

Andrei Iancu
*Director of the United States Patent and Trademark Office*